(12) United States Patent  (10) Patent No.: US 8,977,364 B2
Skaribas et al.  (45) Date of Patent: Mar. 10, 2015

(54) EXTERNAL, HEAD-WORN ELECTRICAL STIMULATOR FOR TREATING HEADACHE CONDITIONS

(71) Applicants: Ioannis Mihail Skaribas, Houston, TX (US); Christopher Atkinson Durst, Houston, TX (US)

(72) Inventors: Ioannis Mihail Skaribas, Houston, TX (US); Christopher Atkinson Durst, Houston, TX (US)

(73) Assignee: Ioannis Mihail Skaribas, Houston, TX (US)

( * ) Notice: Subject to any disclaimer, the term of this patent is extended or adjusted under 35 U.S.C. 154(b) by 0 days.

(21) Appl. No.: 13/875,865

(22) Filed: May 2, 2013

(65) Prior Publication Data

US 2013/0296967 A1  Nov. 7, 2013

Related U.S. Application Data

(63) Continuation of application No. 61/642,105, filed on May 3, 2012.

(51) Int. Cl.
  *A61N 1/04* (2006.01)
  *A61N 1/36* (2006.01)

(52) U.S. Cl.
  CPC .......... *A61N 1/0484* (2013.01); *A61N 1/36021* (2013.01); *A61N 1/0456* (2013.01)
  USPC .............................. 607/46; 607/139; 607/149

(58) Field of Classification Search
  USPC .......................................... 607/139, 46, 149
  See application file for complete search history.

(56) References Cited

U.S. PATENT DOCUMENTS

| 4,233,986 A | 11/1980 | Tannenbaum |
| 4,856,526 A | 8/1989 | Liss et al. |
| 4,967,038 A * | 10/1990 | Gevins et al. ................. 600/383 |
| 5,540,736 A | 7/1996 | Haimovich et al. |
| 6,023,642 A | 2/2000 | Shealy et al. |
| 6,381,481 B1 * | 4/2002 | Levendowski et al. ....... 600/383 |
| 6,554,787 B1 | 4/2003 | Griffin et al. |
| 7,610,095 B2 * | 10/2009 | Naisberg ......................... 607/45 |

(Continued)

FOREIGN PATENT DOCUMENTS

| CA | 2472485 A1 | 2/2004 |
| JP | 2003-339885 | 2/2003 |

(Continued)

OTHER PUBLICATIONS

International Search Report and Written Opinion, dated Sep. 13, 2013, for International Application No. PCT/US2013/039292, International Filing Date May 2, 2013.

*Primary Examiner* — Michael Kahelin

(74) *Attorney, Agent, or Firm* — Conley Rose, P.C.

(57) ABSTRACT

An external, head worn electrical nerve stimulation device, including a power source and a head band configured to fit around a patient's head, the patient's head including a front portion, a rear portion opposite the front portion, a first lateral side, and a second lateral side opposite the first lateral side. The device further includes a plurality of electrical electrodes circumferentially disposed along the head band, wherein the plurality of electrodes contacts each of the front portion, the rear portion, the first lateral side, and the second lateral side. The plurality of electrical electrodes is configured to stimulate, with electrical current, at least one of the greater occipital nerve, the lesser occipital nerve, the supraorbital nerve, the supratrochlear nerve, zygomatotemporal nerve, and the auriculotemporal nerve when the electrodes are energized by the power source.

10 Claims, 15 Drawing Sheets

(56) References Cited

U.S. PATENT DOCUMENTS

| | | |
|---|---|---|
| 7,664,552 B2 | 2/2010 | Wahlstrand et al. |
| 2006/0167526 A1* | 7/2006 | Wan et al. ............ 607/46 |
| 2006/0259094 A1 | 11/2006 | Naisberg et al. |
| 2007/0250145 A1 | 10/2007 | Kraus et al. |
| 2009/0082831 A1 | 3/2009 | Paul et al. |
| 2009/0210028 A1 | 8/2009 | Rigaux et al. |
| 2010/0030299 A1 | 2/2010 | Covalin |

FOREIGN PATENT DOCUMENTS

| | | |
|---|---|---|
| JP | 2003-339885 A | 12/2003 |
| JP | 2011-526180 A | 10/2011 |
| KR | 10-2010-0067603 A | 6/2010 |
| RU | 2131274 C1 | 10/1999 |
| WO | 82/01656 | 5/1982 |
| WO | 2006/044793 A2 | 4/2006 |
| WO | 2006/051370 A1 | 5/2006 |
| WO | 2011/044173 A1 | 4/2011 |

* cited by examiner

EXTERNAL, HEAD-WORN ELECTRICAL STIMULATOR FOR TREATING HEADACHE CONDITIONS

CROSS-REFERENCE TO RELATED APPLICATIONS

This application claims benefit of U.S. provisional patent application Ser. No. 61/642,105 filed May 3, 2012, and entitled "External, Battery-Operated, Head-Worn Electrical Stimulator For Treating Headache Conditions," which is hereby incorporated herein by reference in its entirety.

STATEMENT REGARDING FEDERALLY SPONSORED RESEARCH OR DEVELOPMENT

Not applicable.

BACKGROUND

Headaches are one of the most common pain disabilities suffered by individuals both here in the United States and all over the world. Headaches can involve the entire head (holocephalic), half of the head (hemicranias), or different parts of the head (occipital, temporal, frontal, supraorbital, etc.). Various treatment techniques and procedures have been developed for treating patients with chronic headaches. Many of these procedures involve the use of transcutaneous electrical nerve stimulation (TENS). Traditional TENS utilizes adhesive paddles which are difficult to utilize above the hairline and simultaneously at different parts of the anterior, lateral, and posterior head. Additional interventional procedures have been developed in which neurostimulating electrodes are surgically implanted under the patient's skin in such a manner that they stimulate the occipital nerve, supraorbital nerve, as well as other peripheral nerve branches of the trigeminal nerve plexus via electrical current generated in a battery pack most often implanted in the patient's posterior torso or buttock area. While interventional treatments have proven helpful for many patients who suffer chronic headaches, they still have the main disadvantage of requiring a surgical procedure in order to temporarily or permanently implant the elements that administer the pain relieving electro therapy to the patient. Also, because these devices are surgically implanted, the patient may not simply remove the device when the treatment is not necessary. Further, additional surgery may be required to replace the battery pack.

SUMMARY

The present disclosure relates to an external, head worn electrical nerve stimulation device. In an embodiment, the device comprises a power source. In addition, the device comprises a head band configured to fit around a patient's head, the patient's head including a front portion, a rear portion opposite the front portion, a first lateral side, and a second lateral side opposite the first lateral side. Further, the device comprises a plurality of electrical electrodes circumferentially disposed along the head band, wherein the plurality of electrodes contacts each of the front portion, the rear portion, the first lateral side, and the second lateral side. The plurality of electrical electrodes is configured to stimulate, with electrical current, at least one of the greater occipital nerve, the lesser occipital nerve, the supraorbital nerve, the supratrochlear nerve, zygomatotemporal nerve, and the auriculotemporal nerve when the electrodes are energized by the power source.

Some embodiments are directed to an external, head worn electrical nerve stimulation device. In an embodiment, the device comprises a power source. In addition, the device comprises a head band configured to fit around a patient's head, the patient's head including a front portion, a rear portion opposite the front portion, a first lateral side, and a second lateral side opposite the first lateral side. Further, the device comprises a plurality of electrical electrodes disposed along the head band, wherein the plurality of electrodes contacts at least one of the front portion, the rear portion, the first lateral side, and the second lateral side. The plurality of electrical electrodes is configured to stimulate, with electrical current, at least one of the greater occipital nerve, the lesser occipital nerve, the supraorbital nerve, the supratrochlear nerve, zygomatotemporal nerve, and the auriculotemporal nerve when the electrodes are energized by the power source. The head band is entirely disposed within a head garment.

Other embodiments are directed to an external, head worn electrical nerve stimulation device. In an embodiment, the device comprises a power source. In addition, the device comprises a head band configured to fit around a patient's head, the patient's head including a front portion, a rear portion opposite the front portion, a first lateral side, and a second lateral side opposite the first lateral side. Further, the device comprises a plurality of electrical electrodes circumferentially disposed along the head band, wherein the plurality of electrodes contacts each of the front portion, the rear portion, the first lateral side, and the second lateral side. The plurality of electrical electrodes is configured to stimulate, with electrical current, at least one of the greater occipital nerve, the lesser occipital nerve, the supraorbital nerve, the supratrochlear nerve, zygomatotemporal nerve, and the auriculotemporal nerve when the electrodes are energized by the power source. The head band is entirely disposed within a head garment.

BRIEF DESCRIPTION OF THE DRAWINGS

For a detailed description of exemplary embodiments of the invention, reference will now be made to the accompanying drawings in which.

DETAILED DESCRIPTION

Figure 1:
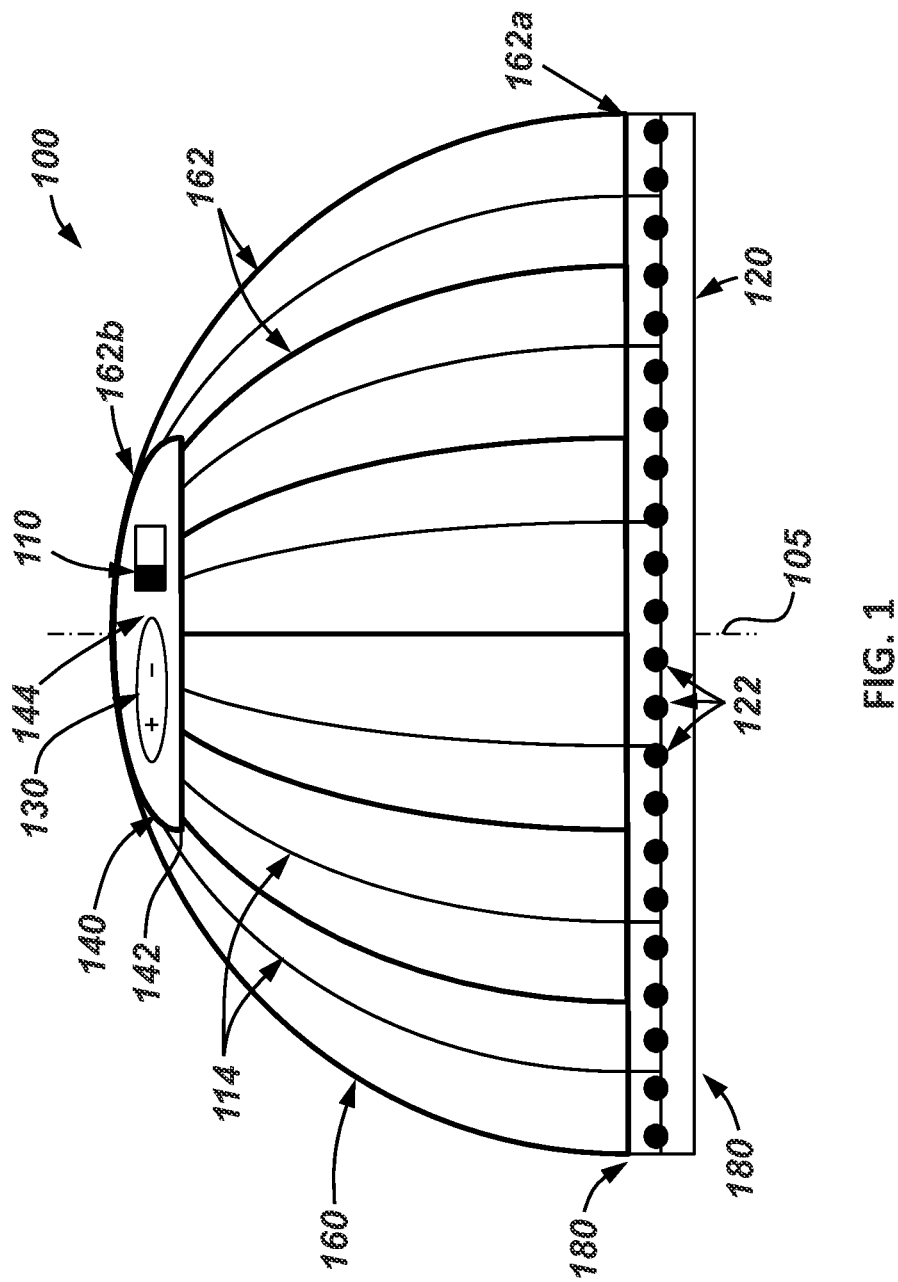
FIG. 1 is a front schematic view of an embodiment of an external, head worn electrical nerve stimulation device in accordance with principles disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

As used herein, the word "approximately" means "plus or minus 10%." In addition, as used herein, the phrase "circumferentially disposed" refers to something that is continuously disposed along a closed geometric shape or surface, whether that shape or surface is elliptical, circular, rectangular, etc. Various embodiments are described herein of an external, head-worn device that provides electrical stimulation to certain specific nerves for treating chronic headache disorders.

Referring to FIG. 1, an embodiment of an external, head worn electrical nerve stimulation device 100 is shown. Device 100 generally includes a central axis 105, a control pack 140, an adjustable frame 160, and a head band assembly 180. Each of these assemblies and components will now be described in more detail below.

Figure 2:
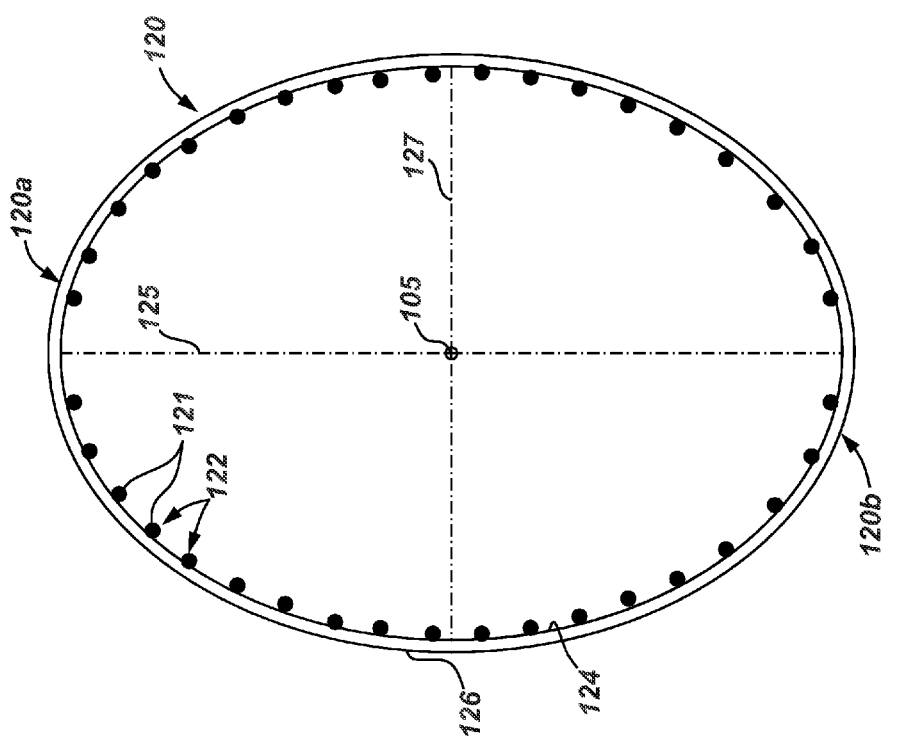
FIG. 2 is a bottom schematic view of the head band and electrodes of the electrical nerve stimulation device of FIG. 1.

Referring now to FIGS. 1 and 2, head band assembly 180 comprises a head band 120 and a plurality of electrical electrode assemblies 122. As will be explained in more detail below, electrode assemblies 122 contact the patient's skin during use and transmit the electrical current thereto to stimulate nerves disposed under the skin to relieve pain. As is best shown in FIG. 2, head band 120 is generally elliptical in shape and includes a major axis 125, a minor axis 127, a first or front side 120a, a second or rear side 120b opposite the front side 120a about the axis 127, a first lateral side 120c, and a second lateral side 120d opposite the first lateral side 120c about the axis 125. Further, head band 120 includes an inner surface 124, and an outer surface 126. The axis 125 is orthogonal to the axis 127 and the axes 125, 127 define a plane that is perpendicular to the axis 105. Head band 120 is configured to fit about a patient's head during operation such that front side 120a corresponds with the front side of the patient's head and rear side 120b corresponds with the back or posterior side of the patient's head. Thus, in at least some embodiments, the size of head band 120 may be adjustable in order to accommodate a wide range of patients. For example, in some embodiments, strap 120 may be adjusted with elastic, buckles, snaps, hook and loop connectors (e.g., VELCRO®), or some combination thereof while still complying with the principles disclosed herein.

As is best shown in FIG. 2, the plurality of assemblies 122 is circumferentially disposed along the inner surface 124. In this embodiment, the plurality of electrode assemblies 122 is disposed along the entire length of surface 124; however, it should be appreciated that in other embodiments, assemblies 122 may only be disposed along a portion of surface 124 or in several discrete portions of surface 124 while still complying with the principles disclosed herein. Also, in this embodiment, each of the electrode assemblies 122 is disposed within a single plane extending substantially perpendicular to axis 105; however, it should be appreciated that in other embodiments assemblies 122 may not be disposed within the same plane. Additionally, in this embodiment, the plurality of electrode assemblies 122 is symmetrically arranged about the axis 125; however, it should be appreciated that in other embodiments, assemblies 122 may not be symmetric about either the axis 125 or the axis 127 while still complying with the principles disclosed herein. Also, in at least some embodiments, assemblies 122 are evenly spaced along surface 124; however, in other embodiments assemblies are not evenly spaced along surface 124. Further, each electrode assembly 122 includes an electrode 121 that is configured to receive and transmit electric current when energized from a power source (e.g., battery). Still further, in this embodiment the assemblies 122 are arranged about head band 120 to stimulate the nerves within the patient's head which are associated with primary or secondary refractory chronic headaches. For example, in some embodiments assemblies 122 are arranged such that electrodes 121 stimulate the greater occipital nerve, the lesser occipital nerve, the supraorbital nerve, the supratrochlear nerve, zygomatotemporal nerve, the auriculotemporal nerve and/or branches of these nerves. It should also be appreciated that in some embodiments assemblies 122 may also be arranged such that electrodes 121 stimulate other peripheral nerves disposed in a patient's head either in lieu of or in addition to the specific nerves listed above while still complying with the principles disclosed herein. Each electrode 121 is configured to contact the bare skin of a patient's head when device 100 is placed thereon. In order to ensure that sufficient contact is achieved along the entire circumference of the patient's head, electrodes 121 may be formed into a variety of shapes and sizes. For example, in this embodiment, electrodes are generally spherical; however, in other embodiments, electrodes 121 may be rectangular, and in still other embodiments, electrodes 121 may be pyramidal all while still complying with the principles disclosed herein.

Figure 4:
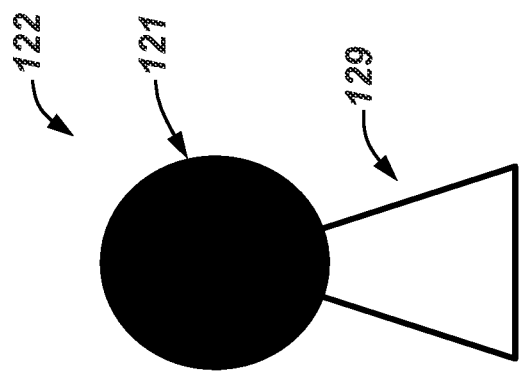
FIG. 4 is a schematic view of an embodiment of one of the electrodes of the electrical nerve stimulation device of FIG. 1.
Figure 3:
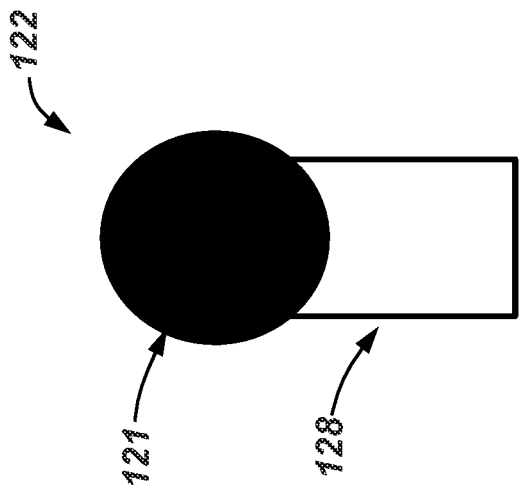
FIG. 3 is a schematic view of an embodiment of one of the electrodes of the electrical nerve stimulation device of FIG. 1.

Referring briefly to FIGS. 3 and 4, because rear side 120b of head band 120 corresponds with the posterior side of a patient's head during operation, electrode assemblies 122 that are disposed along rear side 120b and lateral sides 120c, d of head band 120 are configured to contact the posterior and/or lateral sides of the patient's head. As a result, electrodes 121 associated with these assemblies 122 should extend through hair that is usually present in such regions in order to make sufficient contact with the skin thereunder. Thus, in some embodiments, at least a portion of the assemblies 122 further comprise a base (e.g., 128 or 129) that is coupled to electrode 121 to ensure that sufficient contact between electrode 121 and the patient's skin occurs in these regions. Referring specifically to FIG. 3, in some embodiments, assembly 122 includes a substantially cylindrically shaped base 128 coupled to electrode 121. Referring specifically to FIG. 4, in other embodiments, assembly 122 includes a substantially frustoconically shaped base 129 coupled to electrode 121 However, it should be appreciated that base (e.g., base 128, 129) may comprise a large variety of shapes and sizes while still complying with the principles disclosed herein.

Referring again to FIG. 1, frame 160 is coupled to head band 120 and generally comprises a plurality of adjustable frame members 162. Each member 162 extends axially upward from head band 120, curves radially inward with respect to the axis 105 and includes a first end 162a, and a second end 162b opposite the first end 162a. The first end 162a of each member 162 is coupled to head band 120 while the second end 162b of each member 162 is coupled to control pack 140. Further, in this embodiment, each member 162 has a length extending between the ends 162a, b that is adjustable to accommodate a variety of head sizes and shapes.

Referring still to FIG. 1, control pack 140 further includes an outer housing 142, a power source 130, and a switch 110. In this embodiment, housing 122 is concentrically disposed about the axis 105 and includes an inner hollow region or cavity 144. Power source 130 is disposed within cavity 144 and, as will be described in more detail below, is configured to supply electrical current to electrode assemblies 122 during operation. In this embodiment, power source 130 is a battery; however, it should be noted that source 130 may comprise any suitable source of electric current while still complying with the principles disclosed herein. Switch 110 is also at least partially disposed within the cavity 144 and has a first or open position and a second or engaged position. Further, in this embodiment, when switch 110 is in the engaged position, electric current is allowed to flow from power source 130 to electrode assemblies 122. Conversely, when switch 110 is in the open position, electric current is prevented from flowing from power source 130 to the electrode assemblies 122.

A plurality of electrical conductors 114 extends from the control pack 140 to assemblies 122. In particular, in this embodiment, each of the plurality of conductors 114 is electrically coupled to power source 130 through switch 110 on one end and is also electrically coupled to at least one of the electrodes 121 on assemblies 120 on the other end. Thus, during operation, when switch is in the engaged position, electric current flows from source 130, through conductors 114, to the electrodes 121 on assemblies 122. While a plurality of conductors 114 is shown in the embodiment depicted in FIG. 1, it should be appreciated that in other embodiments, only one conductor 114 may be routed between control pack 140 and assemblies 122 while still complying with the principles disclosed herein. Further, as will be described in more detail below, in at least some embodiments control pack 140 further comprises control logic (not shown) (e.g., microprocessor, central processing unit, etc.) to control the supply of power from source 130 to electrodes 121 during operation based on a pre-determined regiment(s). Still further, in other embodiments, device 100 also include a low battery indicator (not shown) located near switch 110 within cavity 144, on the separate remote (not shown), or some other suitable location along or within device 100 such that the patient will be alerted when the power level within source 130 has fallen below a level that is acceptable for operating the device 100. The low battery indicator may comprise a visual indicator (e.g., a light emitting diode), an audible indicator, or both.

Figure 5:
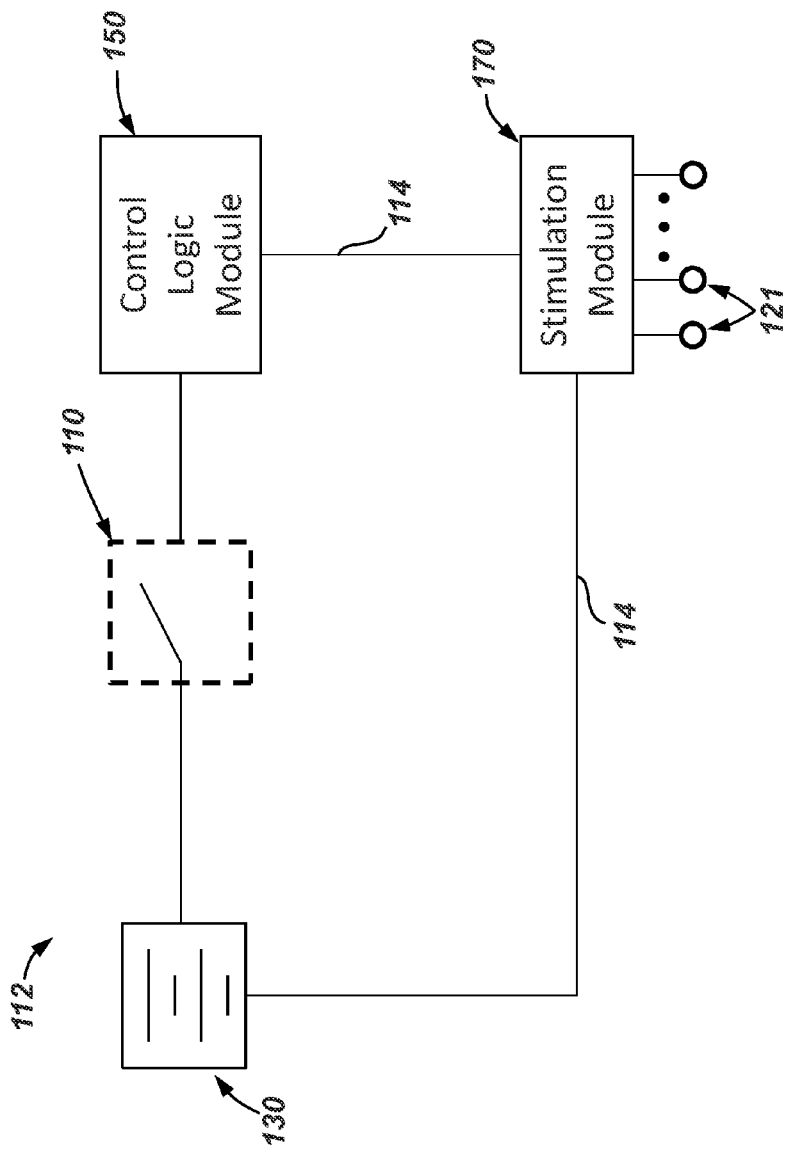
FIG. 5 is a black box circuit diagram a embodiment of a circuit for the electrical nerve stimulation device of FIG. 1.

Referring now to FIG. 5, a black box circuit diagram of an example circuit 112 for use with an external, head worn electrical nerve stimulation device (e.g., device 100) in accordance with the principles disclosed herein is shown. While circuit 112 is described below as being used within device 100, one skilled in the art will appreciate that circuit 112 may be employed within any of the embodiments disclosed herein. In this embodiment, circuit 112 generally includes the power source 130, the switch 110, a controller 150 (e.g., a microprocessor), and a stimulation module 170. During operation, when switch 110 is actuated to the engaged position, previously described, current passes from power source 130, through controller 150, and into stimulation module 170. Controller 150 then alters the current passing therethrough based on control logic disposed therein. In some embodiments, the controller 150 may output electric current for a specified period of time (e.g., 10 to 30 minutes) that has an amplitude that either remains continuous, oscillates, ramps up and maintains a generally stable value, or some combination thereof. In this embodiment, stimulation module 170 generally comprises the electrodes 121 previously described. Thus, when electric current enters stimulation module 170, it is routed to at least a portion of the electrodes 121. As will be described in more detail below, when device 100 is disposed about a patient's head and electrodes 121 are energized as described above, current passes from electrodes 121 into the patient's head to stimulate nerves disposed therein. In some embodiments, the controller 150 may output electric current such that only a portion of the electrodes 121 are energized. Further, in at least some embodiments, power source 130, switch 110, and control logic module 150 are disposed within cavity 144 of control pack 140. Also, in some embodiments the switch 110 may comprise an electro-mechanical switch such as a button, knob, lever, etc. In other embodiments, the switch 110 may also comprise a magnetic tap sensor, or any other type of mechanism to turn the device 100 on and off.

Figure 6:
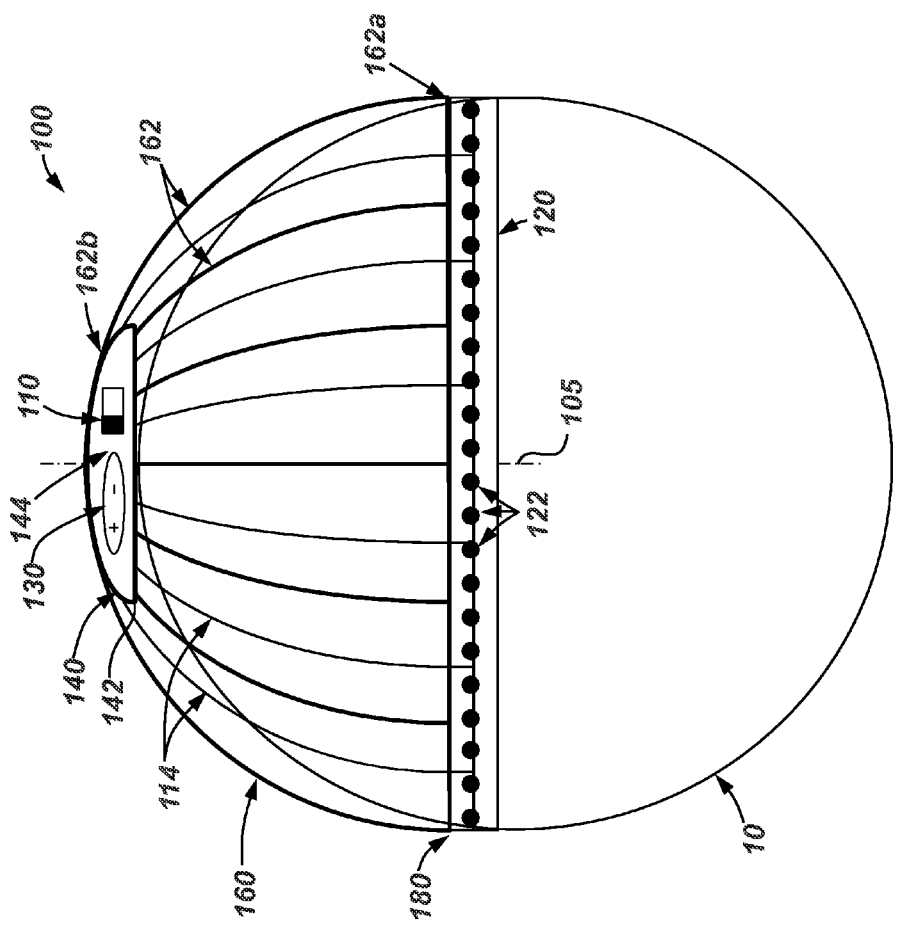
FIG. 6 is a schematic view of the electrical nerve stimulation device of FIG. 1 disposed about a patient's head.

Referring to FIG. 6, during operation the device 100 is placed on the head 10 of a patient suffering from chronic headaches such that frame 160 generally conforms to the curvature of head 10. Device 100 is then activated by, for example, actuating electrical switch 110 to the engaged position thereby allowing electric current to flow from source 130 within control pack 140, through conductors 114, and into electrodes 121 on assemblies 122. Once energized, electrodes 121 transmit current into the specific nerves, previously described, in order to substantially eliminate and/or prevent the pain associated with a headache. In some embodiments, the specific nerve or nerves to be stimulated is determined by the physical placement of electrode assemblies 122 about head band 120, while in other embodiments, the specific nerve or nerves to be stimulated is determined by control logic (e.g., control logic contained in module 150). In particular, in some embodiments, the control logic contained within control pack 140 activates only some of the electrodes 256 in order to target neurostimulation to certain nerves or nerve groups. For example, a patient that is experiencing a primary headache involving one specific set of nerves or a specific region of the head (e.g., an occipital neuralgia-headache located only or primarily in the occiput of the patient's head) may operate the device 100 such that the control logic within pack 140 directs only the electrodes 121 disposed proximate those nerves or regions to perform electrical stimulation. As another example, a patient experiencing a holocephalic headache (i.e. a headache involving the entire head) (e.g., migraines or tension type headaches) may operate the device 100 such that the control logic within pack 140 directs all or substantially all of the electrodes 121 to simultaneously perform electrical stimulation, and all or substantially all peripheral cranial nerves are stimulated at once. Further, and in accordance with one implementation, the neurostimulation may involve an electrical signal with the following characteristics: 5-250 Hz, 1-60 milliamperes, 0-400 volts, and 0-10 milliseconds. In accordance with another implementation, neurostimulation may involve delivering an asymmetric waveform with a frequency of approximately 125 Hz and a pulse width of approximately 125 microseconds. However, it should be appreciated that, in these implementations, the pulse width will vary greatly depending on the signal intensity.

Figure 7:
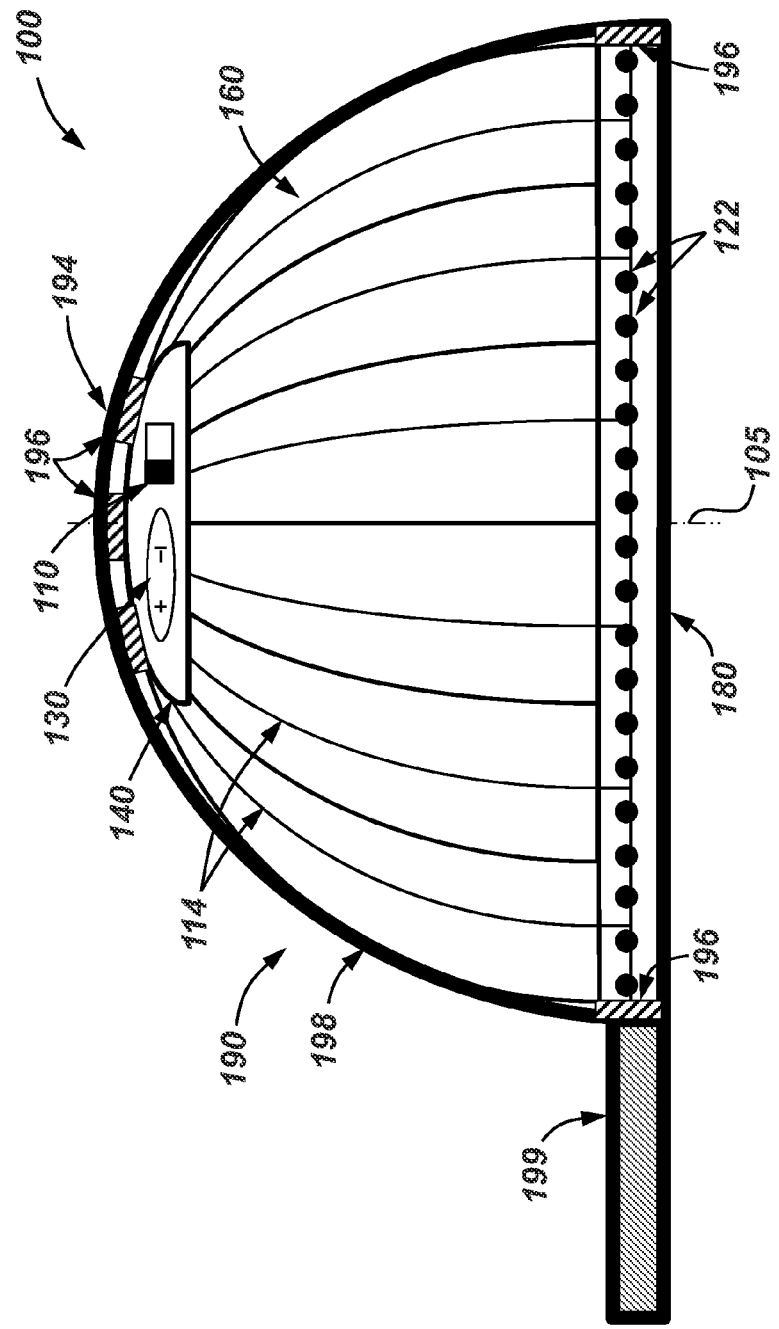
FIG. 7 is a schematic view of the electrical nerve stimulation device of FIG. 1 disposed within a head garment.

Referring now to FIG. 7, in some embodiments, device 100 may be entirely disposed within a head garment 190. Head garment 190 may be any suitable head garment, such as, for example, a baseball cap, Fedora, beret, trilby hat, and a headband while still complying with the principles disclosed herein. In this embodiment, garment 190 is a baseball cap that includes a body 198 and a brim 199. Body 198 comprises a fabric and has a first or outer surface 198a and a second or inner surface 198b defining a cavity 197. As is shown in FIG. 7, in this embodiment, device 100 is releasably secured within body 198 of garment 190 thus concealing device 100 from view. In particular, device 100 is releasably secured within cavity 197 of body 198 of garment 190 with a coupling system 194, which further includes a plurality of coupling members 196 disposed between the surface 198b and the device 100. Members 194 may be any suitable device or system for releasably coupling the device 100 to head garment 190 while still complying with the principles disclosed herein. For example, in some embodiments, coupling members 194 may comprise hook and loop connectors, snaps, straps, buttons, and/or combinations thereof. In this embodiment, the members 194 comprise hook and loop connectors. Additionally, in this embodiment, coupling members 196 are disposed proximate the control pack 140 and assembly 180; however, it should be appreciated that in other embodiments members 196 may be placed at any suitable location between device 100 and the inner surface 198b of body 198 while still complying with the principles disclosed herein. Further, when device 100 is disposed within cavity 197 as shown in FIG. 5, conductors 114 may either be placed along the inner surface of body 198 or, in some embodiments, may be sown or otherwise disposed within the fabric of body 198 itself. Further, in some embodiments, control pack 140 may not be disposed within cavity 197 of hat and may instead be disposed external to cap 190. For example, in some embodiments, control pack 140 may be disposed elsewhere on the patient's person (e.g., clipped on to the patient's belt). Still further, in some of these embodiments, the internal components of control pack 140 may be electrically coupled to electrodes through either through an electrical conductor or a wireless connection (e.g., BLUETOOTH®) while still complying with the principles disclosed herein.

During operation, device 100 is secured within cavity 197 of body 198 as previously described, such that device 100 is substantially hidden from view. Thereafter, the patient activates the device 100 in substantially the same manner as described above, thus relieving and/or preventing the pain associated with headaches. As a result, when device 100 is placed within cavity 197 of a head garment 190 a patient may use device 100 to treat chronic headaches discretely and thus may perform treatments while conducting regularly daily activities.

Figure 8:
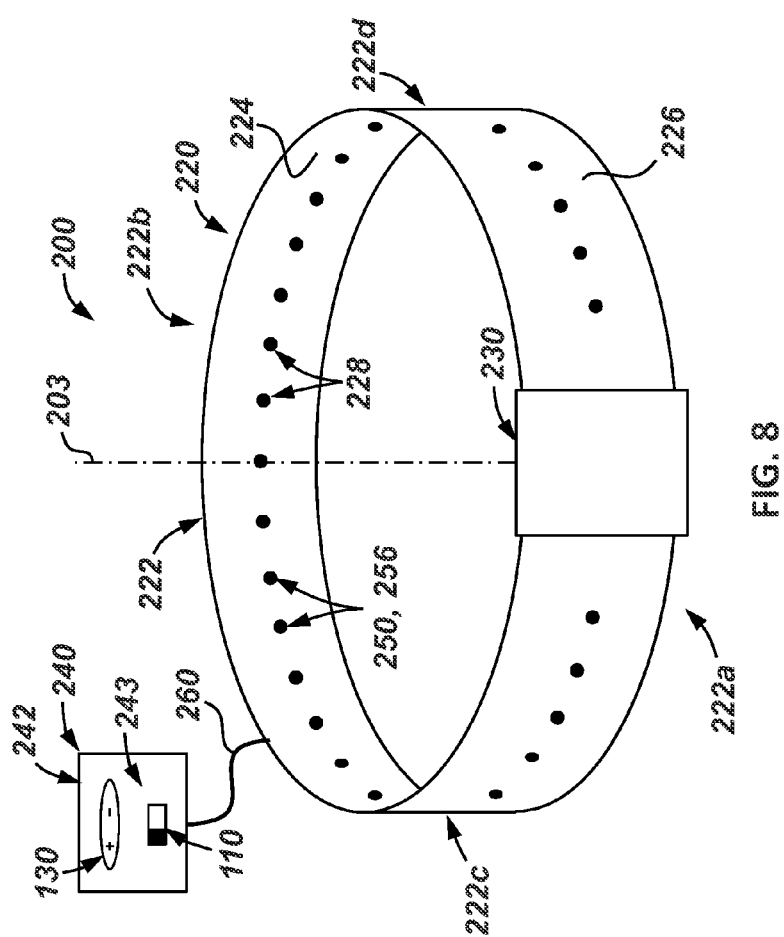
FIG. 8 is a schematic front perspective view of an embodiment of an external, head-worn electrical nerve stimulation device in accordance with the principles disclosed herein.
Figure 9:
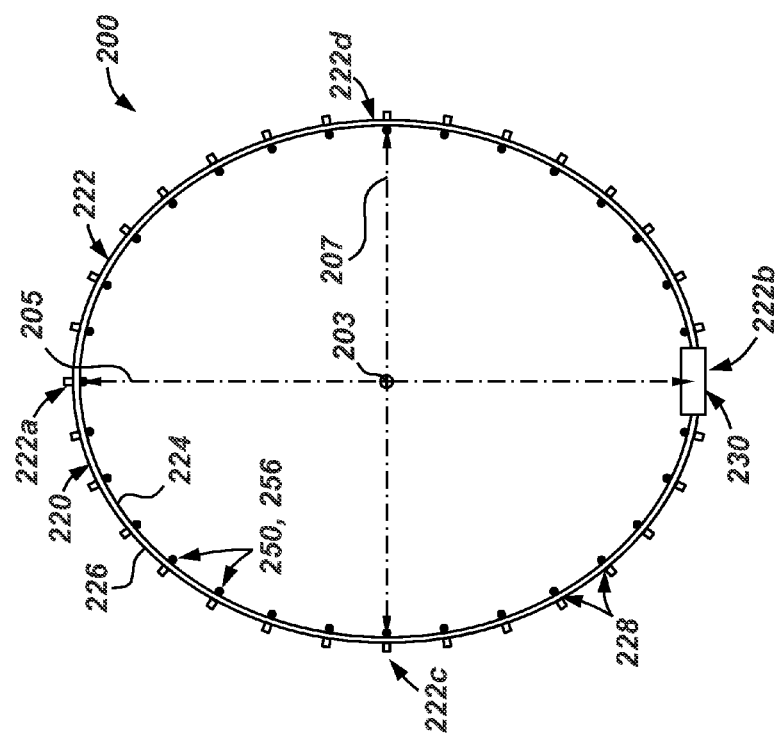
FIG. 9 is a bottom schematic view of the head hand and electrodes of the electrical nerve stimulation device of FIG. 8.

Referring now to FIGS. 8 and 9, an embodiment of an external, head worn electrical nerve stimulation device 200 is shown. In general, device 200 comprises a head band assembly 220 and a control pack 240. Assembly 220 further comprises an elliptically shaped head band 222 and an adjustment assembly 230 coupled to band 222. Band 222 further comprises central axis 203, a major axis 205, a minor axis 205, a first or front side 222a, a second or rear side 222b opposite the front side 222a about the axis 207, a first lateral side 222c, and a second lateral side 222d opposite the first lateral side 222c about the axis 205. Further, band 222 also includes an inner surface 224 and an outer surface 226.

Adjustment assembly 230 is coupled to band 222 along the front portion 122a and is configured to adjust the overall size of band 122 to allow device 200 to accommodate a wide variety of head sizes and shapes. Assembly 230 may be any suitable mechanism for adjusting the size of band 222 while still complying with the principles disclosed herein, such as, for example, a ratchet, straps, hook and loop connectors, buttons, buckles, or some combination thereof. Further, in some embodiments, band 222 may comprise elastic, while in other embodiments, band 222 may be segmented with pivot points disposed between at least some of the individual segments. Still further, in other embodiments, band 222 may include a "scissor link" which includes X-shaped links with pivots allowing adjustment of the length of band 222.

Band 222 also includes a plurality of apertures or holes 228 circumferentially disposed about band 222 and extending between the surfaces 224, 226. As is best shown in FIG. 9, assembly 220 also includes a plurality of electrode assemblies 250, where each assembly 250 is disposed within one of the holes 228 in band 222 and each includes an electrode 256. Further, in this embodiment, assemblies 250 are substantially symmetrically disposed along band 222 about the axes 205, 207 and substantially circumferentially disposed along band 222 about axis 203; however, it should be appreciated that assemblies 250 may not be symmetrically arranged along band 222, while still complying with the principles disclosed herein. For example, in some embodiments, assemblies 250 are only disposed on the front portion 222a, while in other embodiments, assemblies 250 are only disposed along the rear end 222b. Still further, in some embodiments, assemblies 250 may be removably disposed within holes 228 band 222 such that their relative placement may be adjusted to correspond with specific nerves or regions of a patient's head. Additionally, in this embodiment each of the assemblies 250 are disposed within a single plane that extends perpendicularly to the axis 203; however, it should be appreciated that in other embodiments assemblies 250 may not be disposed within a single plane. As is described above for assemblies 122 on device 100, assemblies 250 are configured to stimulate the nerves within the patient's head which are associated with primary or secondary refractory chronic headaches. For example, assemblies 250 may be arranged such that they stimulate the greater occipital nerve, the lesser occipital nerve, the supraorbital nerve, the supratrochlear nerve, zygomatotemporal nerve, the auriculotemporal nerve and/or the branches of these nerves. It should also be appreciated that assemblies 250 may also be arranged to stimulate other peripheral nerves disposed in a patient's head either in lieu of or in addition to the specific nerves listed above while still complying with the principles disclosed herein.

Figure 10:
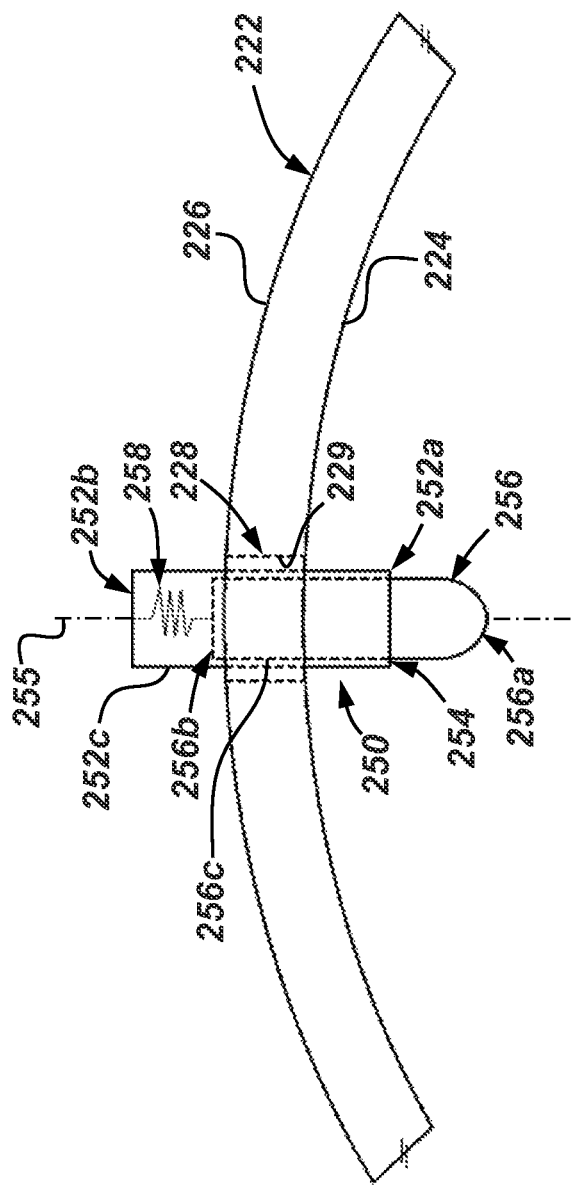
FIG. 10 is an enlarged schematic side view of an embodiment of one of the electrodes disposed within the head band of the electrical nerve stimulation device of FIG. 8.

Referring now to FIG. 10, wherein an embodiment of one of the electrode assemblies 250 is shown disposed within one of the holes 228 in band 222. In this embodiment, electrode 250 comprises an outer housing 252, an electrode 256, and a biasing member 258. Housing 252 further includes a central longitudinal axis 255, a first or inner end 252a, a second or outer end 252b opposite the inner end 252a, a radially outer surface 252c extending axially between the ends 252a, b, and a receptacle or recess 254 extending axially from the inner end 252a. Electrode 256 is disposed within recess 254 along axis 255 and includes a first or inner end 256a and a second or outer end 256a opposite the inner end 256a. Biasing member 258 is disposed within recess 254 and contacts outer end 256b of electrode 256 to bias inner end 256a axially outward from recess 254 during operation. In this embodiment, biasing member 258 is a coiled spring; however, it should be appreciated that in other embodiments biasing member 258 may be any suitable biasing member or mechanism while still complying with the principles disclosed herein. Further, in this embodiment, assembly 250 is installed within hole 228 through engagement of external threads disposed along the radially outer surface 252c of housing 252 and corresponding internal threads disposed along an inner surface 229 of hole 228. Thus, as will be described in more detail below, each assembly 250 may be adjusted within band 222 by rotating housing 252 within the corresponding hole 228 about the axis 255 to advance or withdraw assembly 250 along the axis 255 in order to ensure sufficient contact is achieved between electrode 256 and the skin of the patient during operation.

Figure 11:
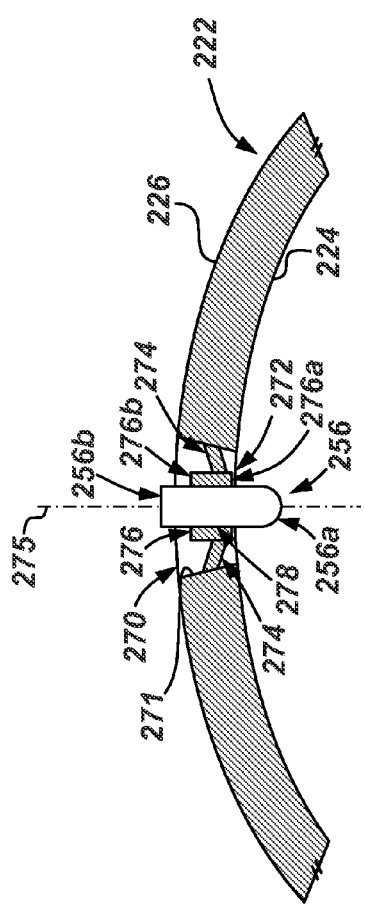
FIG. 11 is an enlarged schematic side view of an embodiment of one of the electrodes disposed within the head band of the electrical nerve stimulation device of FIG. 8.
Figure 12:
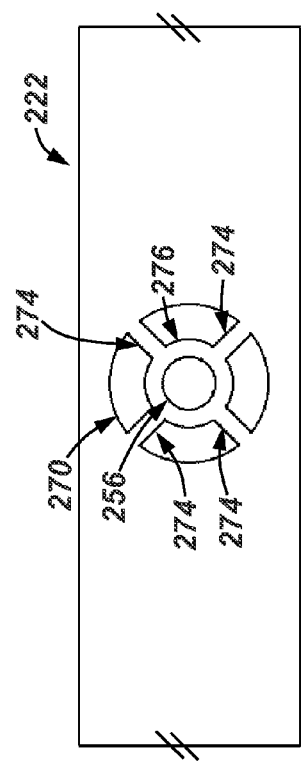
FIG. 12 is a schematic front view of the electrode of FIG. 11.

Referring now to FIGS. 11 and 12, in some embodiments, holes 228 are replaced with holes 270 each defined by an inner surface 271 and further including a self-biasing mounting basket 272. In this embodiment, basket 272 comprises a plurality of suspension biasing arms 274 and a retaining member 276 further housing electrode 256, previously described. Retaining member 276 is generally cylindrical in shape and includes a central axis 275, a first end 276a, a second end 276b opposite the first end 276a, and a central throughbore 278 extending between the ends 276a, b. Electrode 256 is disposed within recess 278 and secured therein by any suitable method. For example, in some embodiments electrode 256 may be threadably engaged within bore 278, while, in other embodiments, electrode may be secured within throughbore 278 through an interference fit. Each of the members 274 extends from the surface 271 of hole 270 to the retaining member 276. Thus, retaining member 276 and electrode 256 are suspended within hole 270 from the members 274. The members 274 are configured to bias retaining member 276 and electrode 256 from the outer surface 226 toward the inner surface 224 of bands 222 such that electrode is biased into engagement with skin of a patient's head during operation. In this embodiment, each of the baskets 272 are monolithically formed with band 222; however, in other embodiments, baskets 272 and band 222 are not monolithically formed while still complying with the principles disclosed herein.

Referring back now to FIG. 8, control pack 240 includes a housing 242 defining a cavity 243, a power source 130, and an electrical switch 110, wherein the power source 130 and switch 110 are the same as previously described above for device 100. In this embodiment, both power source 130 and switch 110 are at least partially disposed within cavity 243 of housing 242. Power source 130 is electrically coupled to electrode assemblies 250 through switch 110 and a conductor 260. Therefore, when switch 110 is in the engaged position as previously described, electric current flows from source 130, through conductor 260, and to electrodes 256 on assemblies 250. Additionally, it should be appreciated that while only one conductor 260 is shown in FIG. 8, in some embodiments, multiple conductors 260 may be routed between control pack 140 and assembly 220 while still complying with the principles disclosed herein.

Figure 13:
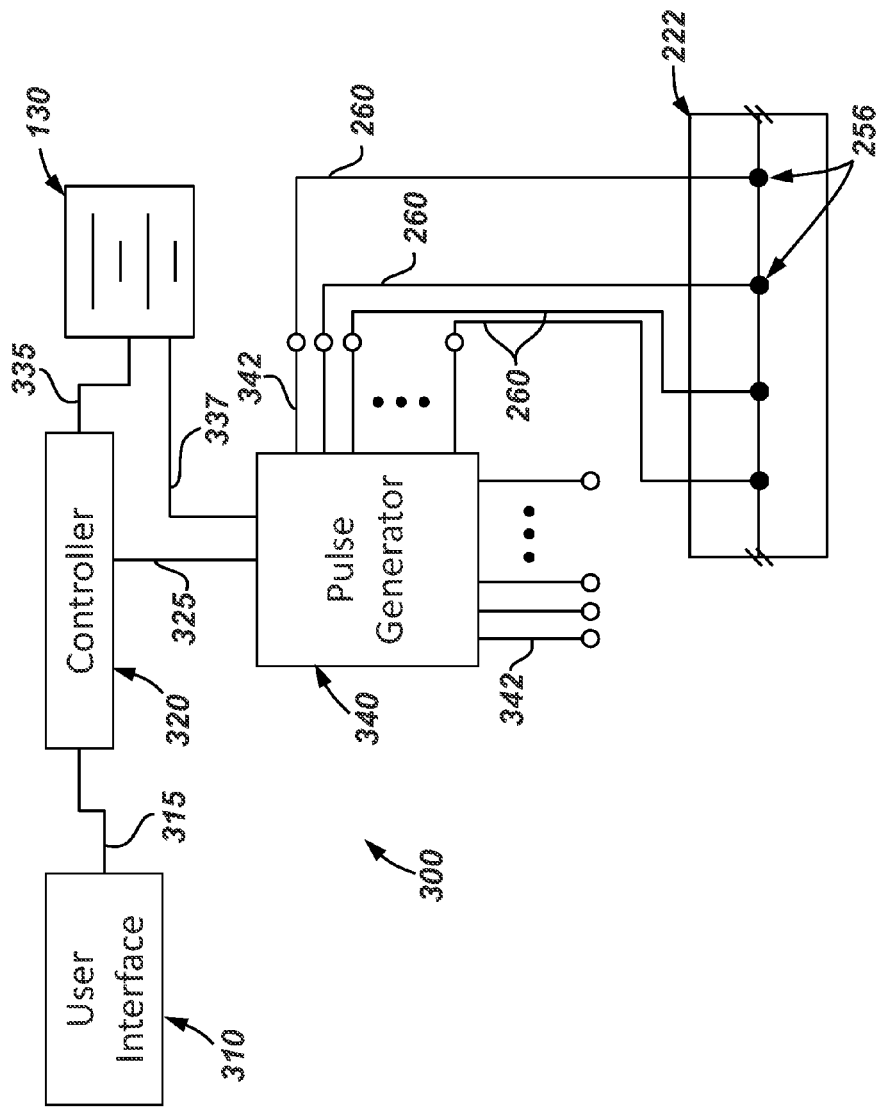
FIG. 13 is a black box circuit diagram of an embodiment of a circuit for use with the electrical nerve stimulation device of either FIG. 1 or 8.

Referring now to FIG. 13, a black box circuit diagram of an example circuit 300 for device 200 is shown. While circuit 300 is described below as being used within device 200, one skilled in the art will appreciate that circuit 300 may be employed within any of the embodiments disclosed herein (e.g., device 100). In this embodiment, circuit 300 includes a user interface 310, a controller 320, a power source 330, previously described, and a pulse generator 340. The controller 320 and pulse generator 340 are electrically coupled to power source 330 through conductors 335, 337, respectively. In addition, in this embodiment, user interface 310 may include a plurality of buttons and/or selection features (not shown) which allow a user (e.g., a patient) to select and/or alter various settings associated with device 200. For example, in some embodiments, interface 310 may include a switch (e.g., switch 110) to turn device 200 on and off. Still further, in at least some embodiments, interface 310, controller 320, pulse generator 340, and power source 130 are all contained within cavity 243 of control pack 240, previously described.

During operation, a user (e.g., a patient) makes adjustments and/or selections through the user interface 310 such that a signal is generated which is routed through a conductor 315 to the controller 320. In some embodiments, controller 320 contains control logic which alters or otherwise processes the signal routed from interface 310. The processed signal is then routed to pulse generator 340 through a conductor 325. Pulse generator 340 comprises a plurality of leads 342 and is configured to generate a series of electrical pulses which are emitted from leads 342 during operation. In this embodiment, at least a portion of the leads 342 are coupled to electrodes 256 on band 222 through a plurality of conductors 260. Thus, after receiving the processed signal from controller 320 through the conductor 325, pulse generator 340 produces a series of electrical pulses which are routed through the conductors 260 to electrodes 256.

Further, each lead 342 on pulse generator 340 may be individually configured as either a negative or a positive lead. Thus, in some embodiments, the controller 320 may direct the pulse generator 340 to emit electrical pulses from leads 342 coupled to electrodes 256 corresponding to a targeted area of the patient's head. During such targeted stimulation, at least one of the electrodes 256 is positively charged and at least one of the electrodes 256 is negatively charged, thus allowing electrical current to pass from the positively charged electrodes 256, through the patient's skin to the negatively charged electrodes 256. Therefore, it is possible to stimulate targeted nerves or nerve groups on the patient's head without having to adjust the placement of band 222. In substantially the same way, the controller 320 may also direct the pulse generator 340 to simultaneously stimulate multiple areas of the patient's head while still complying with the principles disclosed herein. For example, in some embodiments the controller 320 may direct the pulse generator 340 to simultaneously energize electrodes 256 disposed along front side 222a and rear side 222b while not also energizing the electrodes 256 disposed along the first lateral side 222c and the second lateral side 222d. As another example, in some embodiments, the controller 320 may direct the pulse generator 340 to simultaneously energize all of the electrodes 256 disposed along band 222. Moreover, each electrode 256 can be individually selected for stimulation and can be either a positive or a negative electrode 256 as specified by the controller 320 and user interface 310.

Figure 14:
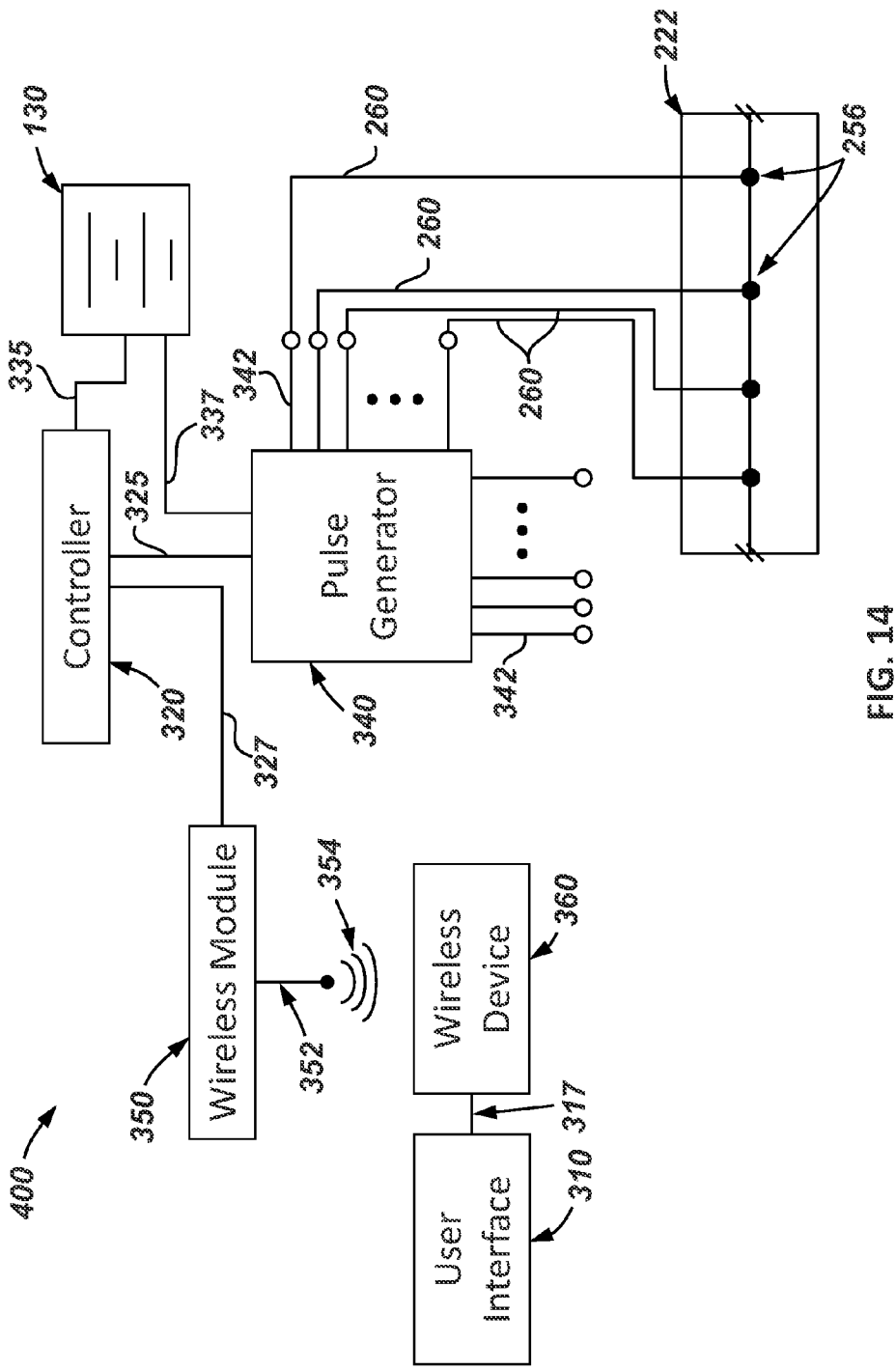
FIG. 14 is a black box circuit diagram of an embodiment of a circuit for use with the electrical nerve stimulation device of either FIG. 1 or 8.

Referring now to FIG. 14, wherein a black box circuit diagram of an example circuit 400 for device 200 is shown. While circuit 400 is described below as being used within device 200, one skilled in the art will appreciate that circuit 400 may be employed within any of the embodiments disclosed herein (e.g., device 100). In general, circuit 400 is substantially the same as the circuit 300, previously described, except that user interface 310 is not directly coupled to controller 320 (e.g., through conductor 315). Instead, circuit 400 includes a wireless module 350 which is coupled to controller 320 through a conductor 345 and a wireless device 360 which is coupled to the interface 310. Wireless module 350 may comprise any device that is capable of generating or receiving a wireless signal (e.g., a wireless radio, BLUETOOTH® enabled device, etc.). In this embodiment, module 350 further includes an antenna 352. Further, wireless device 360 may also comprise any device capable of generating or receiving a wireless signal. In at least some embodiments, device 360 may comprise a smart phone, a tablet device, a computer, etc. In these embodiments, user interface 310 may be implemented by software executing on a processor that is downloaded onto device 360. During operation, a user (e.g., a patient) selects or adjusts a particular setting on interface 310, such that a signal is routed from interface 310 to device 360 which then generates a wireless signal 354 that is received by module 350. Once module 350 receives the signal it is routed to controller 320 through a conductor 327 such that the signal may then be processed and routed as previously described above for circuit 300.

Figure 15:
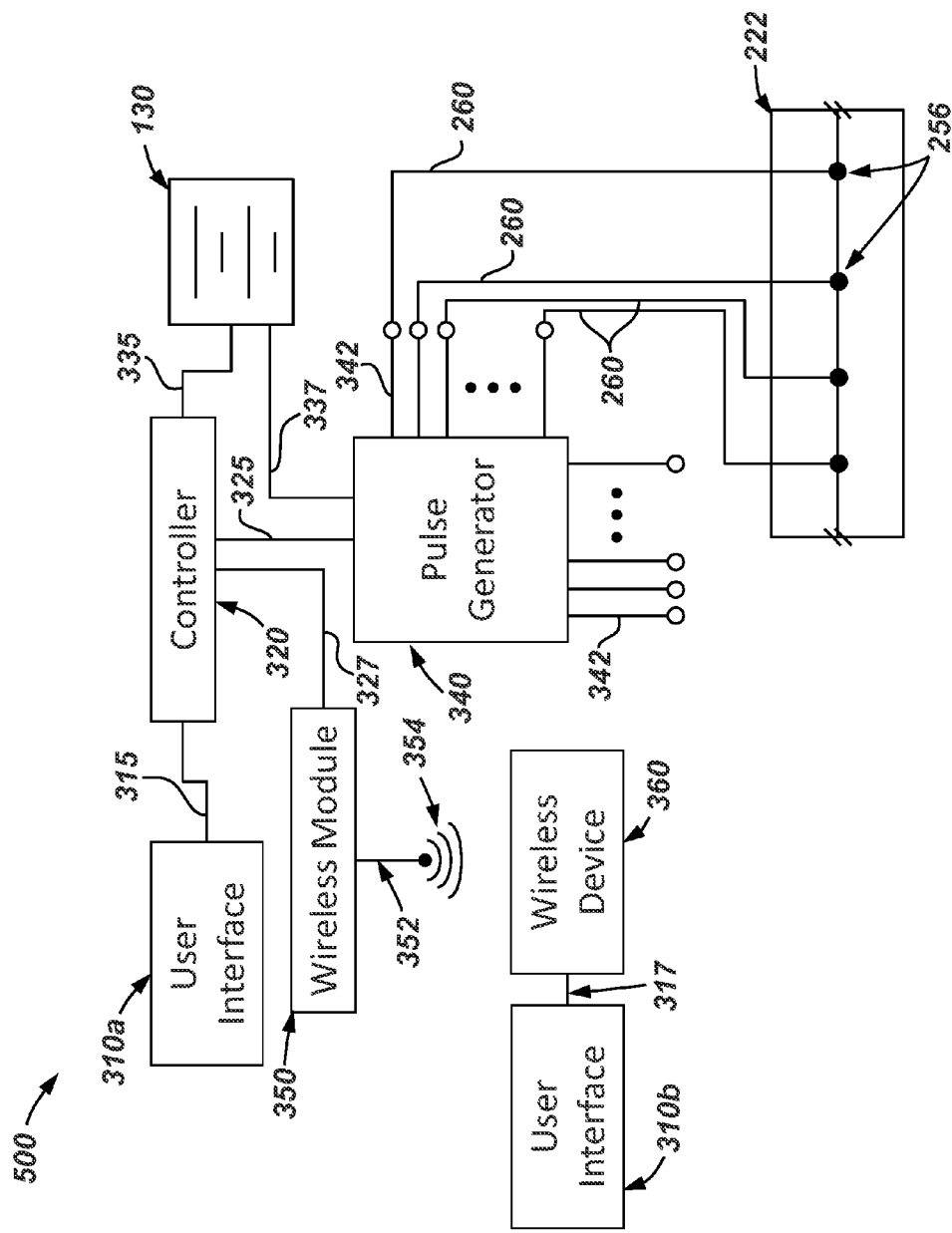
FIG. 15 is a black box circuit diagram of an embodiment of a circuit for use with the electrical nerve stimulation device of either FIG. 1 or 8.

Referring now to FIG. 15, wherein a black box circuit diagram of an example circuit 500 for device 200 is shown. While circuit 500 is described below as being used within device 200, one skilled in the art will appreciate that circuit 500 may be employed within any of the embodiments disclosed herein (e.g., device 100). In general, circuit is substantially the same as the circuit 400 previously described, except that circuit 500 includes a pair of user interfaces 310—a first user interface 310a that is coupled to controller 320 through a conductor 315, and a second user interface 310b that is coupled to wireless device 360 through conductor 317. Thus, during operation, a user may select or adjust a particular setting by manipulating either of the interfaces 310a, b. In particular, a user may select or adjust a particular setting by manipulating the interface 310a such that a signal is routed to controller 320 through conductor 315. Alternatively, a user may select or adjust a particular setting by manipulating the interface 310b such that a signal is routed to controller 320 through device 360, signal 354, module 350, and conductor 327 to controller 320. In either case, once the signal is received by controller 320 it is processed and routed as previously described above for circuit 300.

Further, it should be appreciated that in some embodiments, a user may override the programming within the controller 320 during operations. For example, in some embodiments, a user may immediately end electrical stimulation by some or all of electrodes 256 by pressing a button, switch, etc. disposed on interface 310 or elsewhere. As still another example, in some embodiments, a user may override a preprogrammed sequence of stimulation by some or all of the electrodes 256 by selecting a button, switch, etc. disposed on user interface 310 or elsewhere to receive immediate electrical stimulation from some or all of the electrodes 256. For at least some of these embodiments, a user may be required to confirm their desire to override the programming within the controller 320 in order to prevent unintentional deviation from a treatment schedule.

Figure 16:
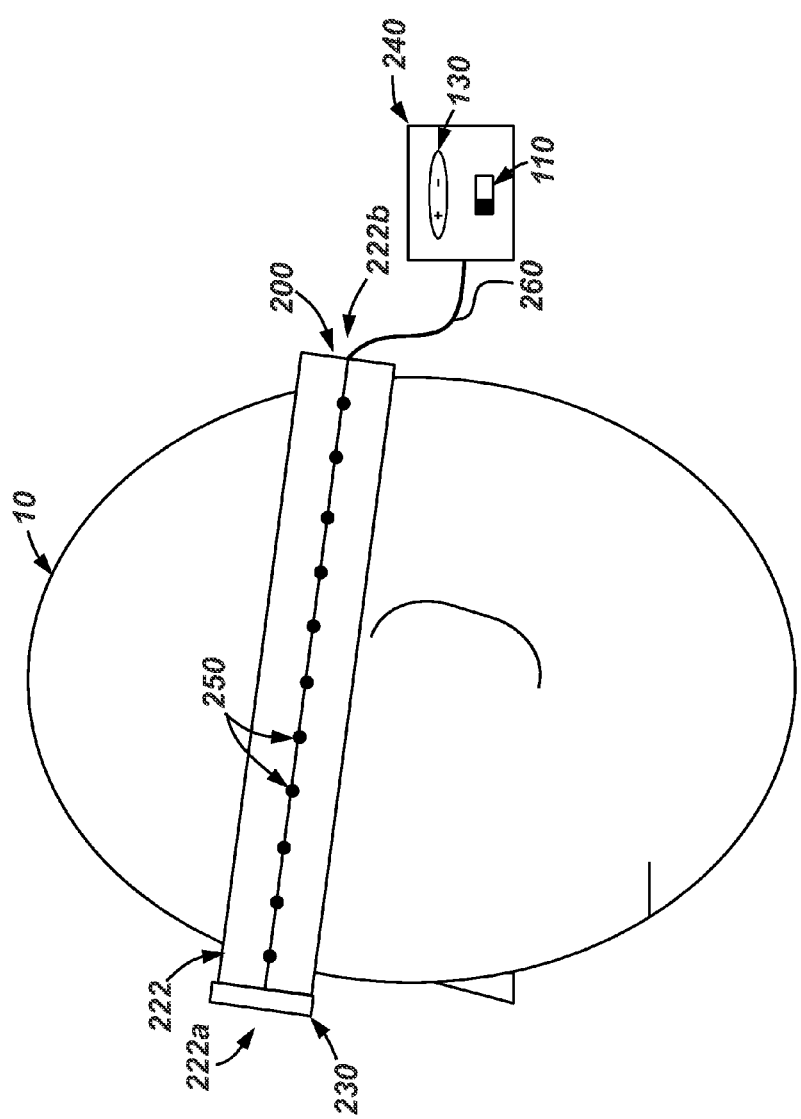
FIG. 16 is a schematic side view of the electrical nerve stimulation device of FIG. 8 disposed about a patient's head.

Referring now to FIGS. 8, 9, and 16, during operation the device 200 is placed on the head 10 of a patient suffering from chronic headaches such that electrodes 256 engage the skin of the patient. In particular, electrodes 256 on assemblies 250 disposed along the front side 222a, rear side 222b, first lateral side 222c, and second lateral side 222d engage the skin of the patient on the frontal portion, the rear portion, the first lateral portion and the second lateral portion of the patient's head, respectively. Device 200 is then activated by actuating electrical switch 110 to the engaged position thereby allowing electric current to flow from source 130 within control pack 240, through conductor(s) 260, and into electrodes 256 on assemblies 250. Once energized, electrodes 256 transmit current into the specific nerves, previously described, in order to substantially relieve and/or prevent the pain associated with a headache. In some embodiments, the specific nerve or nerves to be stimulated is determined by the physical placement of electrode assemblies 250 about head band 222, while in other embodiments, the specific nerve or nerves to be stimulated is determined by control logic (e.g., control logic contained in controllers 150, 320). In particular, in some embodiments, control logic contained within control pack 240 activates only some of the electrodes 256 in order to target neurostimulation to certain nerves or nerve groups. For example, a patient that is experiencing a primary headache involving one specific set of nerves or a specific region of the head (e.g., an occipital neuralgia-headache located only or primarily in the occiput of the patient's head) may operate the device 200 such that only the electrodes 256 disposed proximate those nerves or regions perform electrical stimulation. As another example, a patient experiencing a holocephalic headache (i.e. a headache involving the entire head) (e.g., migraines or tension type headaches) may operate the device 200 such that all or substantially all of the electrodes 256 simultaneously perform electrical stimulation, and all or substantially all peripheral cranial nerves are stimulated at once. In accordance with one implementation, the neurostimulation may involve an electrical signal with the following characteristics: 5-250 Hz, 1-60 milliamperes, 0-400 volts, and 0-10 milliseconds. In accordance with another implementation, neurostimulation may involve delivering an asymmetric waveform with a frequency of approximately 125 Hz and a pulse width of approximately 125 microseconds. However, it should be appreciated that, in these implementations, the pulse width will vary greatly depending on the signal intensity.

Figure 17:
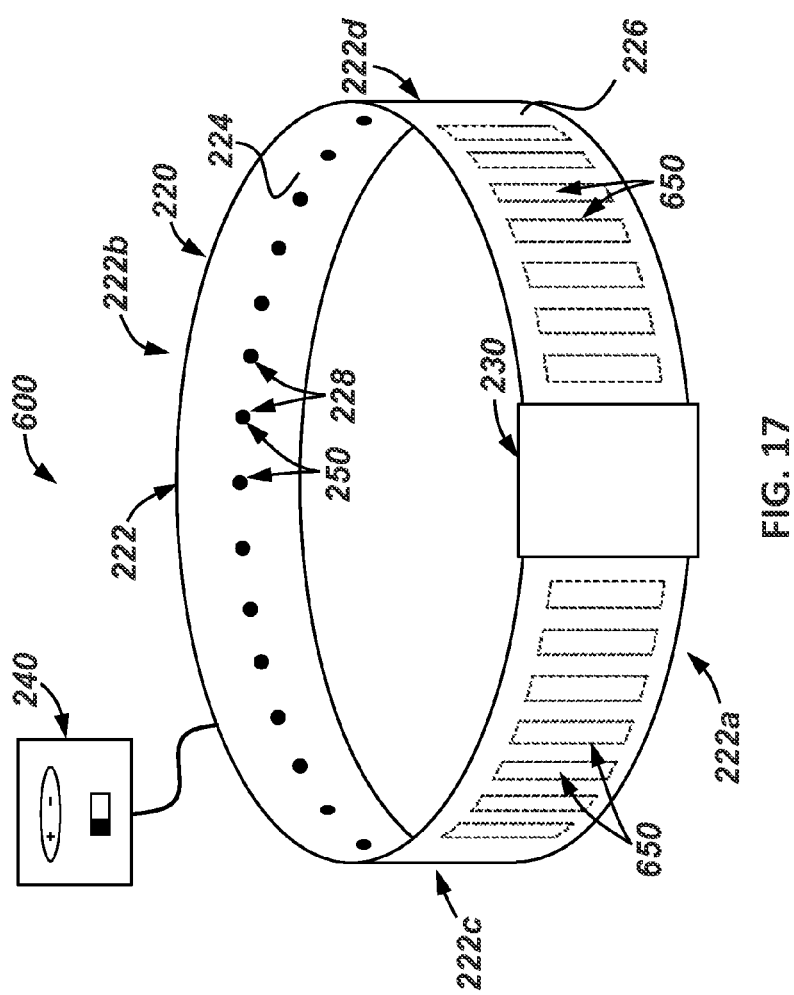
FIG. 17 is a schematic front perspective view of an embodiment of an external, head-worn electrical nerve stimulation device in accordance with the principles disclosed herein.

Referring now to FIG. 17, wherein an embodiment of an external, head word electrical nerve stimulation device 600 is shown. In general, device 600 is substantially the same as the device 200 previously described. As a result, like parts are designated with like reference numerals. However, device 300 does not include holes 128 or electrode assemblies 150 on along the front portion 222a of band 222 and instead includes a plurality of strips of conductive fabric 650 disposed along front portion 222a of band 222. Conductive fabric 650 may be any conformal material that may transfer electric current therethrough (e.g., a silver-plated conductive fabric). For example, in some embodiments, conductive fabric 650 may comprise MEDTEX 180 available from Marktek, Inc. located in Chesterfield, Mo. Each strip of conductive fabric 650 is configured to receive electric current from source 130 through conductor 260 in the same manner as previously described above for the assemblies 250. In particular, during operation, each strip 650 receives electric current from source 130 such that the current may be emitted through strip into the patients head to stimulate nerves disposed thereunder. In some embodiments, all or substantially all of the assemblies 250 may be replaced with strips of conductive fabric 650 while still complying with the principles disclosed herein.

Through use of an embodiment of an external, head worn electrical nerve stimulation device (e.g., device 100, 200, and 600) in accordance with the principles disclosed herein, a patient may electrically stimulate nerves associated with primary or secondary refractory chronic headaches, and thus may reduce and/or prevent the pain associated therewith. In addition, through use of an external, head worn electrical nerve stimulation device in accordance with the principles disclosed herein, a patient may stimulate nerves associated with primary or secondary refractory chronic headaches without needing to undergo a surgical procedure or having to implant any device underneath the skin. Further, in some embodiments (e.g., device 100) a patient may discretely treat primary or secondary refractory chronic headaches by placing or disposing the entire device within a head garment. Still further, through use of an embodiment of external, head worn electrical nerve stimulation device in accordance with the principles disclosed herein, one may stimulate, with electric current, the entire circumference of a patient's head, thus treating true holocephalic primary headaches such as migraines, tension type headaches, or trigeminal cephalalgias.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. An external, head worn electrical nerve stimulation device, comprising:
    a power source;
    a head band configured to fit around a patient's head, the patient's head including a front portion, a rear portion opposite the front portion, a first lateral side, and a second lateral side opposite the first lateral side; and
    a plurality of electrical electrodes disposed along the head band, wherein the plurality of electrodes is configured to simultaneously contact each of the front portion, the rear portion, the first lateral side, and the second lateral side, and wherein each of the plurality of electrodes is disposed within a single plane that extends through the patent's head when the head band is installed thereon;
    wherein the plurality of electrical electrodes is configured to simultaneously stimulate, with electrical current, each of the greater occipital nerve, the lesser occipital nerve, the supraorbital nerve, the supratrochlear nerve, zygomatotemporal nerve, and the auriculotemporal nerve when the head band is installed on the patient's head and when the electrodes are energized by the power source.

2. The device of claim 1, wherein the head band and the power source is entirely disposed within a head garment.

3. The device of claim 2, wherein the head band is releasably secured within the head garment with a plurality of coupling members.

4. The device of claim 3, wherein the plurality of coupling members comprises a plurality of hook and loop connectors.

5. The device of claim 1, further comprising a controller, wherein the controller is configured to energize only a portion of the electrodes.

6. The device of claim 1, wherein the plurality of electrodes includes:
    a first electrode configured to contact the front portion;
    a second electrode configured to contact the front portion;
    a third electrode configured to contact the first lateral side; and
    a fourth electrode configured to contact the second lateral side;
    wherein the controller is configured to simultaneously energize the first electrode, the second electrode, the third electrode, and the fourth electrode.

7. The device of claim 1, wherein at least a portion of the electrodes comprise conductive fabric.

8. The device of claim 1, wherein at least a portion of the electrodes are disposed on a base; wherein the base is configured to extend the electrode through hair disposed on the patient's head.

9. A hat configured to be disposed on a person's head, the hat comprising:
    a body defining a cavity;
    a headband coupled to the body and disposed within the cavity, wherein the head band is configured to fit around the persons head, the person's head including a front portion, a rear portion opposite the front portion, a first lateral side, and a second lateral side opposite the first lateral side; and
    a plurality of electrical electrodes circumferentially disposed along the head band, wherein the plurality of electrodes is configured to contact each of the front portion, the rear portion, the first lateral side, and the second lateral side, and wherein each of the plurality of electrodes is disposed within a single plane that extends through the patent's head when the hat is installed thereon;
    wherein the plurality of electrical electrodes is configured to simultaneously stimulate, with electrical current, each of the greater occipital nerve, the lesser occipital nerve, the supraorbital nerve, the supratrochlear nerve, zygomatotemporal nerve, and the auriculotemporal nerve when the electrodes are energized by a power source.

10. The hat of claim 9, further comprising a controller, wherein the controller is configured to energize only a portion of the electrodes.

* * * * *